(12) United States Patent
Nguyen et al.

(10) Patent No.: US 11,806,701 B2
(45) Date of Patent: Nov. 7, 2023

(54) USE OF MONOPROPYLENE GLYCOL FROM PURGE STREAMS IN EPOXIDATION CATALYST PREPARATION

(71) Applicant: Lyondell Chemical Technology, L.P., Houston, TX (US)

(72) Inventors: Ha H. Nguyen, Houston, TX (US); Anthony S. Dearth, Houston, TX (US); Harold V. Larson, Houston, TX (US)

(73) Assignee: Lyondell Chemical Technology, L.P., Houston, TX (US)

( * ) Notice: Subject to any disclaimer, the term of this patent is extended or adjusted under 35 U.S.C. 154(b) by 42 days.

(21) Appl. No.: 17/358,775

(22) Filed: Jun. 25, 2021

(65) Prior Publication Data

US 2021/0402386 A1 Dec. 30, 2021

Related U.S. Application Data

(60) Provisional application No. 63/044,409, filed on Jun. 26, 2020.

(51) Int. Cl.
| | |
|---|---|
| *B01J 37/04* | (2006.01) |
| *B01J 23/28* | (2006.01) |
| *B01J 37/00* | (2006.01) |
| *B01J 37/08* | (2006.01) |
| *C07D 301/19* | (2006.01) |

(52) U.S. Cl.
CPC ............... *B01J 37/04* (2013.01); *B01J 23/28* (2013.01); *B01J 37/009* (2013.01); *B01J 37/08* (2013.01); *C07D 301/19* (2013.01)

(58) Field of Classification Search
CPC . B01J 37/04; B01J 37/009; B01J 37/08; B01J 23/28; C07D 301/19
See application file for complete search history.

(56) References Cited

U.S. PATENT DOCUMENTS

| | | | |
|---|---|---|---|
| 3,434,975 | A | 3/1969 | Sheng et al. |
| 3,574,772 | A | 4/1971 | Mecker et al. |
| 4,661,463 | A | 4/1987 | Mocella |
| 5,599,955 | A | 2/1997 | Vora et al. |
| 5,723,637 | A | 3/1998 | Tsuji et al. |
| 8,389,750 | B2 | 3/2013 | Sawyer |

FOREIGN PATENT DOCUMENTS

| | | |
|---|---|---|
| CN | 102898276 A | 1/2013 |
| CN | 102453003 B | 5/2014 |
| EP | 2108639 A1 | 10/2009 |
| EP | 2277834 B1 | 4/2015 |

OTHER PUBLICATIONS

The International Search Report and Written Opinion for PCT/US2021/039133 dated Oct. 29, 2021.

*Primary Examiner* — Coris Fung
*Assistant Examiner* — Catriona M Corallo

(57) ABSTRACT

Methods for preparing molybdenum-based catalyst for epoxidation reactions using MPG sourced from a propylene oxide/styrene monomer (POSM) production process are described. Streams exiting from the POSM reactor are combined and separated to isolate an aqueous-based, MPG-containing purge stream from other recoverable byproducts of the POSM process. This MPG-containing purge stream is then used as is in the catalyst preparation of molybdenum-based catalyst for epoxidation. Alternatively, the MPG-containing purge stream can undergo additional purification treatments before being utilized in the catalyst preparation.

20 Claims, 2 Drawing Sheets

USE OF MONOPROPYLENE GLYCOL FROM PURGE STREAMS IN EPOXIDATION CATALYST PREPARATION

PRIOR RELATED APPLICATIONS

This application claims the benefit of priority to U.S. Provisional Patent Application No. 63/044,409, filed on Jun. 26, 2020, which is incorporated herein by reference in its entirety.

FEDERALLY SPONSORED RESEARCH STATEMENT

Not applicable.

REFERENCE TO MICROFICHE APPENDIX

Not applicable.

FIELD OF THE DISCLOSURE

The disclosure relates generally to molybdenum-based catalyst. Specifically, monopropylene glycol-containing purge streams from a propylene oxide/styrene monomer production process are used in the preparation of molybdenum-based catalysts.

BACKGROUND OF THE DISCLOSURE

Molybdenum-based catalysts are widely used in both the oil and gas and polymer fields due to their variety of applications. These catalysts can be used in hydrotreating of hydrocarbon-containing fluids to remove sulfur, as well as in acrolein oxidation, methanol oxidation, propene selective oxidation, and olefin metathesis reactions necessary to synthesize many different polymers and plastics.

A growing application of molybdenum-based catalysts is for the indirect epoxidation of olefins, particularly to form propylene oxide (PO). PO is in strong demand due to its use in the synthesis of both flexible and rigid polyurethanes. PO has been used in bedding, furniture, carpeting, coatings, building materials, automotive components, and adhesives. In fact, PO production increased 3.5% per year from 2010-2016.

Propylene oxide/styrene monomer (POSM) production technology is used for about a third of the world's production of propylene oxide. The POSM production process reacts propylene and ethylbenzene hydroperoxide in the presence of a molybdenum-based epoxidation catalyst to produce PO and styrene, as well as a number of other 'waste' products. The ratio of PO to styrene is about 1:2.5 in the POSM production process.

Another indirect epoxidation method of producing PO using a molybdenum-based catalyst is the Propylene Oxide/t-Butyl Alcohol (POTBA) technology. In a POTBA process, propylene oxide and t-butyl alcohol (TBA) are produced by reacting a t-butyl hydroperoxide and propylene. The ratio of PO to t-butyl alcohol is about 1:2 in the POTBA process.

Regardless of the epoxidation method, the amount of co-product is always much greater than the PO. Thus, PO producers have to contend with the dependence of product price on the fluctuating market for PO and the co-products for an economic process. The demand for styrene has not kept up with PO, with the consumption of styrene increasing by 1.7% per year from 2010-2016. TBA's demand is growing as it can be converted into high-octane gasoline components such as methyl tert-butyl ethyl and ethyl tertiary butyl ether, and high purity isobutylene which is used in tires and lubricants. Further, PO producers also have to consider the cost, energy consumption and capital expenditures associated with treating or disposing of waste streams exiting the POSM and POTBA processes.

Many improvements have been made to reduce the costs associated with producing PO while meeting market demand. However, there still exists a need for further improvements as even incremental changes in technology can mean the difference between a cost-effective PO production process, and cost prohibitive energy and production losses.

SUMMARY OF THE DISCLOSURE

The present disclosure provides an improved method for producing molybdenum-based epoxidation catalysts used in propylene oxide production. The improved method utilizes an aqueous-based purge stream from the propylene oxide/styrene monomer (POSM) production process as a source of monopropylene glycol (MPG). This aqueous-based purge stream can be utilized as is (i.e. untreated) in the preparation of the molybdenum-based catalyst or pretreated to increase the purity of MPG. The catalyst prepared using this MPG source can then be used in propylene oxide/t-butyl alcohol (POTBA) production processes. The improved methods result in a more cost-effective PO production by reducing the cost associated with catalyst preparation and reducing the cost associated with treating the purge streams.

The present methods include any of the following embodiments in any combination(s) of one or more thereof:

A molybdenum epoxidation catalyst composition comprising a molybdenum metal powder, a peroxy compound, a solvent, and monopropylene glycol (MPG) from an MPG-containing purge stream from a Propylene Oxide/Styrene Monomer (POSM) production process.

The above composition, wherein the MPG is present in an amount of about 1 to about 15 weight percent.

Any of the above compositions, wherein the MPG-containing purge stream is an untreated purge stream.

Any of the above compositions, wherein the MPG-containing purge stream is a treated purge stream.

Any of the above compositions, wherein the MPG-containing stream has been treated to reduce water content and concentrate the MPG.

A method for preparing a molybdenum-based epoxidation catalyst comprising feeding one or more purge streams from a Propylene Oxide/Styrene Monomer (POSM) production process into a reactor, wherein the purge streams contain monopropylene glycol (MPG). Molybdenum metal powder, a peroxy compound, and a solvent are then added to the reactor to react with the MPG to produce a molybdenum epoxidation catalyst. The molybdenum epoxidation catalyst can then be isolated from the other reaction products.

A method for preparing a molybdenum-based epoxidation catalyst comprising preparing an MPG-containing stream from at least one exit stream recovered from a POSM production process. To prepare the MPG-containing stream, one or more streams exiting a POSM reactor are directed to a settling tank, where the streams are combined before being separated into an aqueous-based purge stream and an organic-based purge stream. The aqueous-based purge stream comprises the MPG, and α-methyl benzyl alcohol, benzaldehyde, acetophenone, or a combination thereof. In some embodiments, this untreated MPG-containing aqueous-based purge stream undergoes liquid-liquid extraction(s) in a liquid-liquid extraction unit with an organic extraction liquid to form an aqueous-based extraction stream and an organic extraction stream, wherein the aqueous-based extraction stream contains the MPG, and a lesser amount of α-methyl benzyl alcohol, benzaldehyde, acetophenone, or a combination thereof than the untreated MPG-containing aqueous-based purge stream. This treated MPG-containing aqueous-based extraction stream can undergo further preparation steps to concentrate the MPG and remove water by coalescing the aqueous-based extraction stream in a coalescer, treating the coalesced output with activated carbon, and drying with a drying apparatus. Once the MPG-containing stream is prepared, it can be fed into a reactor and reacted with molybdenum metal powder, a peroxy compound, and a solvent that are also in the reactor to produce a molybdenum epoxidation catalyst. The molybdenum epoxidation catalyst can then be isolated from the other reaction products.

Any of the above compositions or methods, wherein the molybdenum metal powder is present in an amount of about 0.5 to 1.0 grams.

Any of the above compositions or methods, wherein the peroxy compound is present in an amount of about 5 to 10 grams.

Any of the above compositions or methods, wherein the peroxy compound is an organic hydroperoxide, hydrogen peroxide or an organic peracid.

Any of the above compositions or methods, wherein the peroxy compound is t-butyl hydroperoxide (TBHP) or t-butyl hydroperoxide (TBHP) oxidate.

Any of the above compositions or methods, wherein the solvent is present in an amount of about 50 to 100 grams.

Any of the above compositions or methods, wherein the solvent is t-butyl alcohol (TBA), isooctane (2,2,4-trimethylpentane), ethyl acetate, benzene.

Any of the above compositions or methods, wherein the solvent is t-butyl alcohol (TBA).

Any of the above methods, wherein the MPG-containing stream has been treated to reduce water content and concentrate the MPG before being fed into the reactor.

Any of the above methods, wherein the MPG-containing stream has been treated to reduce the amount of α-methyl benzyl alcohol, benzaldehyde, and/or acetophenone before being fed into the reactor.

Any of the above methods, wherein the MPG-containing stream has been treated to reduce the amount of α-methyl benzyl alcohol, benzaldehyde, acetophenone, and/or water before being fed into the reactor.

Any of the above methods, wherein the total concentration of MPG in the purge streams is from about 30 to about 75 weight percent.

Any of the above methods, wherein the amount of MPG in the reaction mixture is from about 1 to about 15 weight percent.

Any of the above compositions or methods, wherein the weight ratio of molybdenum metal powder to the peroxy compound is between about 1:5 to 1:20, the weight ratio of molybdenum metal powder to the solvent is between about 1:50 to 1:200, and the weight ratio of molybdenum metal powder to the MPG is between about 1:50 to about 1:200.

Any of the above compositions or methods, wherein the molybdenum metal powder is present in an amount of about 0.5 to 1.0 grams, the peroxy compound is present in an amount of about 5 to 10 grams, the TBA is present in an amount of about 50 to 100 grams.

Any of the above compositions or methods, wherein the molybdenum metal powder is present in an amount of about 0.5 to 1.0 grams, the peroxy compound is present in an amount of about 5 to 10 grams, the TBA is present in an amount of about 50 to 100 grams, and the MPG is present in an amount of about 1 to about 15 weight percent.

Any of the above compositions or methods, wherein the molybdenum metal powder is present in an amount of about 0.5 to 1.0 grams, the peroxy compound is TBHP and is present in an amount of about 5 to 10 grams, the TBA is present in an amount of about 50 to 100 grams.

Any of the above compositions or methods, wherein the molybdenum metal powder is present in an amount of about 0.5 to 1.0 grams, the peroxy compound is TBHP and is present in an amount of about 5 to 10 grams, the TBA is present in an amount of about 50 to 100 grams, and the MPG is present in an amount of about 1 to about 15 weight percent.

Any of the above methods, wherein the organic extraction liquid is ethylbenzene, n-octane, toluene, or combinations thereof.

This summary is provided to introduce a selection of concepts that are further described below in the detailed description. This summary is not intended to identify key or essential features of the claimed subject matter, nor is it intended to be used as an aid in limiting the scope of the claimed subject matter.

DEFINITIONS

Figure 1:
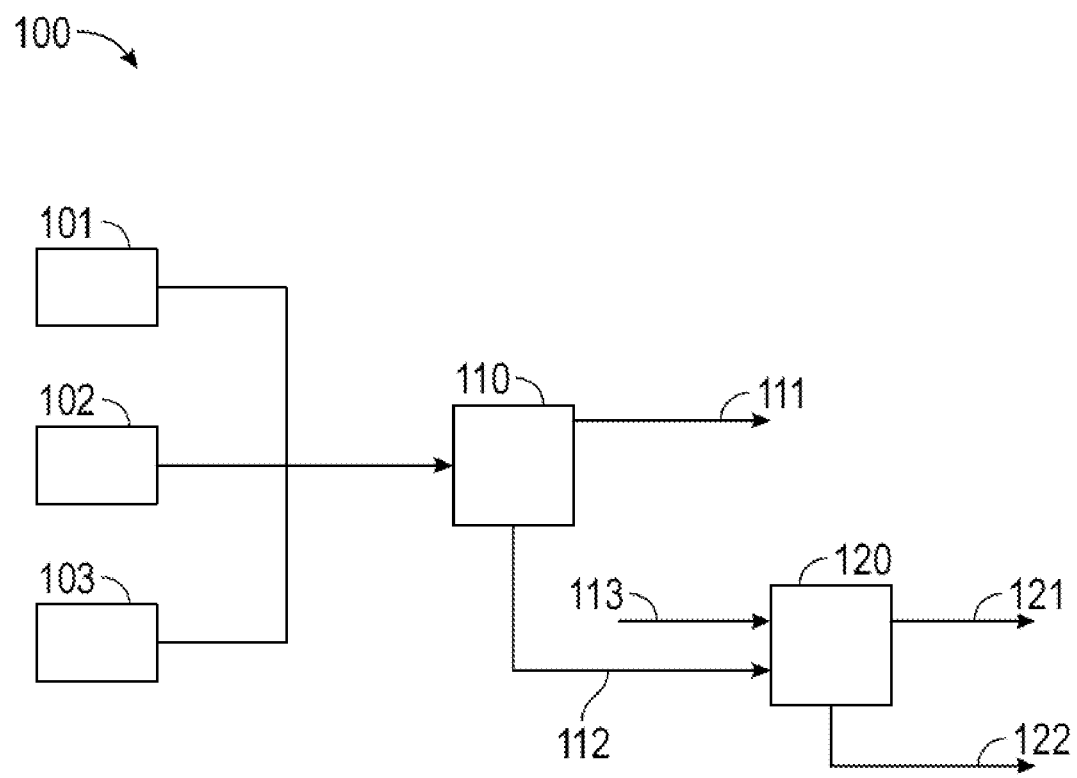
FIG. 1. depicts a schematic of a system for recovering MPG from one or more streams exiting a POSM production process.

The term "clean" when used in conjunction with MPG refers to a purity level of at least 95 wt % of MPG. The term "pure" when used in conjunction with MPG refers to a reagent grade purity level of MPG, which has at least 99 wt % of MPG.

A stream exiting the POSM reactor is referred to herein as an "exit" or "exiting" stream. The exiting streams undergo a gravity-based separation using a "settling tank" to separate organic and aqueous components. The term "settling tank" refers to a vessel that uses gravity and differences in density to separate two or more components. As used herein, one or more fluid mixtures exiting a POSM reactor are introduced into the settling tank, wherein heavier components such as an aqueous phase sink to the bottom under the influence of gravity, leaving the lighter, mostly organic phase as a top layer. In some embodiments, heavier recoverable organic components, also referred to herein as "heavies", will sink to the bottom with the aqueous phase. Exemplary "heavies" include, but are not limited to, benzaldehyde, α-methyl benzyl alcohol, acetophenone, or combinations thereof. The light, organic based layer and the heavy, aqueous-based layer can be removed separately from the settling tank as "purge streams".

The heavier, aqueous-based purge stream is a monopropylene glycol-containing stream. The aqueous-based purge stream exiting the settling tank is also referred to herein as "untreated MPG purge stream", "untreated purge stream", or "untreated MPG-containing stream". The untreated MPG purge stream can be used as is once it is removed from the settling tank in the presently disclosed methods to prepare the Mo-based epoxidation catalyst. Alternatively, the untreated MPG purge stream can undergo further treatment and purification steps to remove heavies, excess water, or other similar components to concentrate the amount of MPG in the purge stream. The term "treated" as it applies to the MPG-containing streams refers to treatment or purification steps to reduce or remove heavies, excess water, or other similar components, and/or to concentrate the MPG. The phrases "treated MPG purge stream", "treated purge stream", and "treated MPG-containing stream" are used interchangeably to refer to the untreated MPG purge stream after it has undergone one or more treatment or purification steps.

The term "coalescer" refers to a device used to separate emulsions into their components via various processes. In the present methods, the coalescer is used in a purification step to remove water from MPG-containing purge streams. The coalescer may include any apparatus that is configured to facilitate and/or promote the coalescence of small particles and/or droplets of MPG into larger particles and/or droplets. In some embodiments of the present disclosure, the coalescer may include a mechanical coalescer or an electrostatic coalescer.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention.

The following abbreviations are used herein:

| ABBREVIATION | TERM |
| --- | --- |
| MPG | monopropylene glycol |
| PO | propylene oxide |
| POSM | propylene oxide and styrene monomer |
| POTBA | propylene oxide/t-butyl alcohol |
| TBA | t-butyl alcohol |
| TBHP | t-butyl hydroperoxide |
| wt % | weight percent |
| XRF | X-Ray Fluorescence |

DESCRIPTION OF EMBODIMENTS OF THE DISCLOSURE

The present disclosure provides improved methods for preparing molybdenum-based catalysts for the Propylene Oxide/t-Butyl Alcohol (POTBA) production process. Specifically, the Mo-based catalysts are prepared using MPG sourced from an aqueous-based purge stream from a Propylene Oxide/Styrene Monomer (POSM) production process. This allows for a cost efficient POSM and POTBA production process because a POSM purge stream is being recycled as a source reactant for the POTBA catalyst. Further, the presence of water in the aqueous-based purge stream can increase the dissolution rate of the molybdenum resulting in a more efficient catalyst preparation process.

In some embodiments, the aqueous-based purge streams can be treated before the catalyst preparation process to reduce the amount of water and organic impurities in the aqueous-based purge stream. While the catalyst preparation process is not affected by the water content, the end use of the catalyst may be affected. In some POTBA processes, for example, too much water can impact the selectivity in the epoxidation reaction. Thus, treatment steps such as a series of liquid/liquid extractions and/or vacuum distillations may be performed on the aqueous-based purge stream.

Molybdenum-based catalysts give high yields of epoxides in the liquid phase oxidation of olefins with organic hydroperoxides. However, the epoxidation of olefins is carried out in an organic solvent, typically an alcohol, thus requiring a catalyst that is soluble in the reaction medium. For the presently disclosed methods, any catalyst preparation process capable of generating molybdenum-based epoxidation catalyst that are soluble in an organic solvent from monopropylene glycol can be used. Suitable molybdenum-based catalyst preparation conditions may be found in U.S. Pat. No. 3,434,975, which is incorporated herein by reference in its entirety for all reasons.

U.S. Pat. No. 3,434,975 relies on the reaction of inexpensive, metallic molybdenum with a peroxy compound and MPG at temperatures ranging between about 25° C. and 100° C. MPG has a high boiling point allowing for this reaction to be carried out at atmospheric pressures. However, the reaction can be carried out under pressure to ensure the reactants are in the liquid phase throughout the preparation process. In some embodiments, the temperature range is between about 25° C. and 50° C., about 60° C. and 80° C., about 75° C. and 100° C., about 40° C. and 70° C. or about 60° C. The reaction time ranges from a few minutes at higher temperatures to several hours at lower temperatures. In some embodiments, the reaction time is between about 15 minutes and 60 minutes, about 45 minutes and 90 minutes, about 60 minutes and 100 minutes, or about 45 minutes and 2 hours.

The molybdenum metal may be in the form of lumps, sheets, foil or powder. In some embodiments, powdered molybdenum material is used because it has a low cost and the greatest surface per unit volume. In the present methods, powdered molybdenum with a particle size that is small enough to pass through an opening of 0.074 mm (about 200 mesh sieve on the Standard Screen Scale) may be used.

The peroxy compound is an organic hydroperoxide, hydrogen peroxide or an organic peracid, each of which is a liquid at the reaction conditions. The quantities of the reactants vary over wide ranges, however, a weight ratio of molybdenum metal to the peroxy compound in the range of from about 1:5 to 1:20. Alternatively, the weight ratio of molybdenum metal to the peroxy compound is about 1:12.5.

The structure of the organic hydroperoxides used in the catalyst preparation method is ROOH, wherein R may be alkyl, alkenyl, aryl, alkaryl, aralkyl, cycloalkyl, cycloalkenyl and similar radicals which also contain functional groups. Examples of such hydroperoxides include, but are not limited to, t-butyl hydroperoxide, t-amyl hydroperoxide, cumene hydroperoxide, tetralin hydroperoxide, alpha-hydroperoxy diisopropyl ketone, the hydroperoxide of Z-methylbutene-Z, the hydroperoxide of octene-1, the hydroperoxide of 2,6-di-tertiary butyl paracresol, and the like.

Exemplary peracids include, but are not limited to, performic acid, peracetic acid, trifluoroperacetic acid, perbenzoic acid and the like.

In some embodiments, the peroxy compound is t-butyl hydroperoxide (TBHP). TBHP converts into the corresponding alcohol upon its reduction, which can be a solvent for the subsequent epoxidation reaction. Alternatively, the peroxy compound is peracetic acid. In yet another alternative, the peroxy compound is hydrogen peroxide in a 20 wt % to 40 wt % solution, or a 20 wt % to 30 wt % percent solution, or a 30 wt % to 40 wt % solution, or a 30 wt % solution.

In some embodiments, the reaction is performed in the presence of a solvent. Exemplary solvents used in the catalyst preparation method include, but are not limited to, t-butyl alcohol (TBA), isooctane (2,2,4-trimethylpentane), ethyl acetate, benzene and the like. In some embodiments, TBA is used. The weight ratio of molybdenum metal to the solvent is in the range of from about 1:50 to 1:200.

U.S. Pat. No. 3,434,975 utilizes clean MPG (at least 95 wt %) in the molybdenum-based catalyst preparation reaction. Alternatively, pure MPG, having a purity level of at least 99 wt % of MPG, is used. The weight ratio of molybdenum metal to MPG can vary over a wide range between about 1:50 to about 1:200. Alternatively, the amount of MPG is from about 1 to about 15 wt %, about 4 to about 12 wt %, about 4 to about 6 wt %, about 8 to about 12 wt %, or about 5 to about 10 wt %.

Exemplary catalyst preparation reaction mixtures can include about 0.5 to 1.0 grams of a molybdenum metal powder; about 5 to 10 grams of a t-butyl hydroperoxide (TBHP) oxidate; about 50 to 100 grams of TBA; and, about 1 to 15 weight percent, or about 0.5 to 13 grams of MPG. The catalyst preparation reaction mixtures optionally contain up to about 20 grams of water.

Alternatively, the catalyst preparation reaction mixture has about 0.6 grams of a molybdenum metal powder; about 7.5 grams of TBHP oxidate; about 60 grams of TBA; and, about 5.7 grams of MPG. Water may be present in an amount of about 19 wt %.

In yet another alternative, the catalyst preparation reaction mixture has about 0.6 grams of a molybdenum metal powder; about 7.5 grams of TBHP oxidate; about 60 grams of TBA; and, about 6 grams of MPG. Water may be present in an amount of about 2.7 wt %.

Once the reaction is complete, the catalyst can be purified and isolated from the other reaction products using any method known in the art. In some embodiments, the catalyst is isolated by filtering the catalyst solution to remove undissolved metallic molybdenum before the catalyst is used in the POTBA process. Additional steps for purifying the molybdenum-based catalyst can also be performed before the POTBA process.

The presently disclosed methods improve upon the catalyst preparation methods in U.S. Pat. No. 3,434,975 by using an inexpensive source of MPG, specifically MPG from a POSM production process. Not only does this MPG source reduce the cost associated with preparing the molybdenum-based catalyst, it also reduces the cost associated with treating or disposing the MPG-containing purge stream from the POSM production process.

The MPG-containing stream is the aqueous-based purge stream exiting the POSM production process. The composition of the untreated aqueous-based purge stream exiting the settling tank in the POSM process has about a 25 to 75 wt % of MPG and can contain about 15 to about 75% water, in addition to recoverable organic compounds (1-50 wt %). The amount of MPG used during the molybdenum-based catalyst preparation reaction does not change even though the source, and purity, of MPG has changed. The untreated MPG-containing stream was unexpectedly found to be a suitable source for the catalyst preparation even though its purity levels were much lower than the about 95 wt % or above that was previously used by U.S. Pat. No. 3,434,975. Further, the resulting catalyst had the same performance ability in the epoxidation reactions as catalysts prepared from clean or pure MPG.

In some embodiments of the presently disclosed methods, however, the untreated MPG-containing stream can be treated before the catalyst preparation methods to increase the concentration of MPG while reducing the amount of heavies or water. Some epoxidation reactions require high selectively. If the amount of water in the MPG-containing stream is too high, it can dilute the overall catalyst solution and negatively impact selectively during the epoxidation. As such, MPG-containing purge streams having a water content above 75% may undergo one or more treatment methods (e.g. series of vacuum distillations) to reduce the water content in some embodiments. In some embodiments, the untreated MPG-containing stream is treated until a water content of about 0-75%, about 0-50%, about 5-75%, about 5-40%, about 10-35%, about 25-50%, about 35-60%, or about 50-75% is obtained.

As mentioned above, the MPG is sourced from one or more streams exiting the POSM process. The POSM production process generates multiple exiting streams that contain one or more recoverable organic chemicals, including, but not limited to, MPG, α-methyl benzyl alcohol, benzaldehyde, and/or acetophenone. These exiting streams are treated as waste streams that require additional capital and energy to dispose of Thus, the presently disclosed methods mitigate these costs by using the MPG-containing purge stream in the POTBA process.

Methods for recycling these exiting streams as a fuel and/or purifying to obtain a final commercial product were disclosed by the Applicant in U.S. Ser. No. 62/844,539, which is incorporated herein in its entirety for all purposes. There, at least one stream exiting the POSM process was introduced into a settling tank and separated into an organic-based purge stream that was recycled back to the POSM process and an aqueous-based purge stream. The aqueous-based purge stream, which comprises MPG among other recoverable organic chemicals, optionally undergoes a series of liquid-liquid extractions using one or more organic extraction streams to separate and purify out the recoverable organic chemicals, thus concentrated the MPG. After the extractions, the final aqueous-based extraction stream can be coalesced before being treated with activated carbon to remove impurities and dried with a drying column or similar apparatus to isolate MPG from water.

In the present methods, the aqueous-based purge stream recovered from the settling tank can be used as is (an untreated MPG purge stream) or can undergo optional purification steps to reduce the content of other recoverable organic chemicals or water (a treated MPG purge stream).

Figure 2:
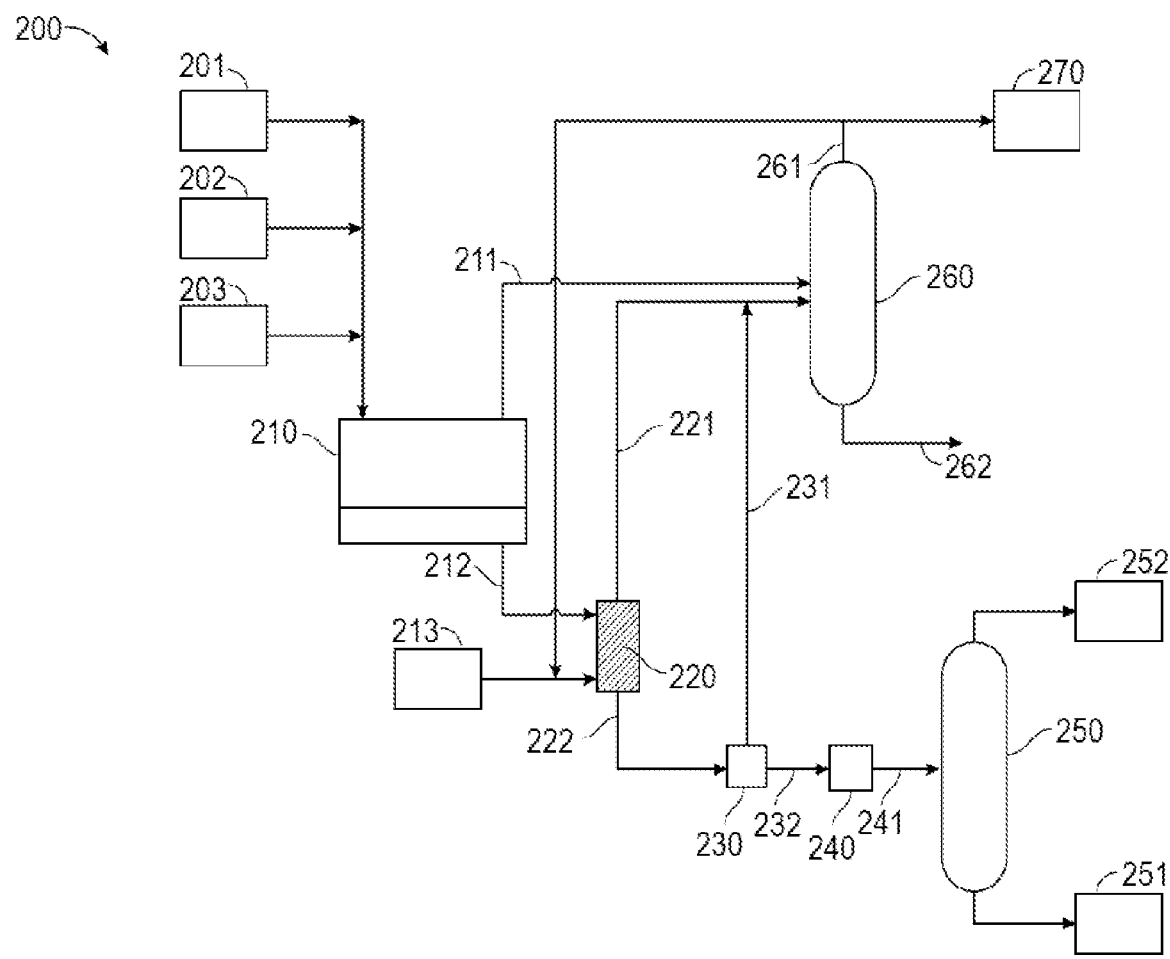
FIG. 2. depicts a schematic of an alternate system for recovering MPG from one or more streams exiting a POSM production process. This alternate system includes one or more purification steps to increase the concentration of MPG.

One embodiment of a system for obtaining the MPG-containing purge stream for the preparation of a Mo-based catalyst is shown in FIG. 1. The system 100 has a settling tank 110 and a liquid-liquid extraction unit 120. Three exiting streams (101, 102, 103) from the POSM process are combined in the settling tank 110, which then separates the streams into an organic-based stream 111 and an aqueous-based stream 112. The organic-based stream 111 can be purified (as shown in FIG. 2), recycled into the POSM process as is, or both purified and recycled into the POSM process.

The aqueous-based stream 112 comprises MPG, water, and other recoverable organic chemicals such as α-methyl benzyl alcohol, benzaldehyde, and acetophenone. This stream 112 can be used "as is" in the preparation of the Mo-based catalyst for the POTBA process as an untreated MPG purge stream.

Alternatively, the aqueous-based stream 112 can undergo additional treatment to reduce the amount of water and/or other recoverable organic chemicals to form a treated MPG purge stream. FIG. 1 displays the process for further treating the aqueous-based stream 112 using liquid-liquid extraction to reduce the content of the other recoverable organic chemicals (e.g. benzaldehyde, α-methyl benzyl alcohol, acetophenone). The aqueous-based stream 112 and an organic extraction liquid 113 are introduced into the liquid-liquid extraction unit 120. The organic extraction liquid 113 can be any organic non-polar solvent. In some embodiments, the organic extraction liquid is an aromatic non-polar solvent such as ethyl benzene, n-octane, toluene, or a combination thereof.

The contacting and subsequent separation of the aqueous-based stream 112 and the organic extraction liquid 113 produces an organic extraction stream 121 and an aqueous extraction stream 122. The aqueous extraction stream 122 comprises MPG and lesser amounts of α-methyl benzyl alcohol, benzaldehyde, and acetophenone. The aqueous extraction stream 122 may be subjected to further purification, such as the liquid-liquid extract steps described herein to further reduce the α-methyl benzyl alcohol, benzaldehyde, and acetophenone.

The aqueous extraction stream 122 can be used as is in the presently disclosed catalyst preparation methods or can undergo additional treatments to isolate MPG from water using the system shown in FIG. 2. Similar to the system in FIG. 1, the system 200 includes a settling tank 210 and a liquid-liquid extraction unit 220. The liquid-liquid extraction unit 220 may be a counter current liquid-liquid extraction unit having a packed-bed style. The three exiting streams (201, 202, 203) from the POSM process are combined in the settling tank 210, which separates the mixture into an organic-based stream 211 and an aqueous-based stream 212. The weight ratio of the organic-based stream 211 to the aqueous-based stream 212 in the settling tank is about 50-70:30-50. In some embodiments, the weight ratio of the organic-based stream 211 to the aqueous-based stream 212 in the settling tank is 65:35.

The organic-based stream 211 from the settling tank 210, the organic extraction stream 221 from the liquid-liquid extraction unit 220, and the organic material 231 from the coalescer 230 are directed to a column 260 that separates the combined streams into a first stream 261 (that includes the organic extraction liquid 213 and styrene) and a second stream 262 that includes some of the heavier recoverable organic chemicals (e.g., benzaldehyde, α-methyl benzyl alcohol, acetophenone, or a combination thereof). The first stream 261 exiting column 260 is recycled in the liquid-liquid extraction unit 220 or recycled into the POSM process 270. The second stream 262 exiting column 260 is used as fuel and/or recycled to the POSM process 270.

The aqueous-based stream 212 comprises MPG, among other recoverable organic chemicals. As before, the aqueous-based purge stream 212 can undergo one or more treatment and/or purification steps to form a treated MPG purge stream. In FIG. 2, the aqueous-based purge stream 212 undergoes a liquid-liquid extraction with an organic extraction liquid 213 in the liquid-liquid extraction unit 220. The contacting and subsequent separation of the aqueous stream 212 and the organic extraction liquid 213 produces an organic extraction stream 221 and an aqueous extraction stream 222. The aqueous extraction stream 222 is then introduced into a coalescer 230, which removes organic material 231 from the aqueous extraction stream 222 to produce a coalesced aqueous extraction stream 232. The coalesced aqueous extraction stream 232 is then contacted with an activated carbon bed 240 to produce a cleaned coalesced aqueous extraction stream 241, which is then directed to a drying column 250 to isolate an MPG-containing stream 251 from water 252. This isolated MPG-containing stream 251 has a lower concentration of water than the MPG-containing aqueous extraction stream 122 or the aqueous-based purge stream 112. The lower water content in MPG-containing stream 251 allows for the preparation of a Mo-based catalyst with improved selectivity during the epoxidation reaction.

The systems in FIGS. 1 and 2 provide both untreated MPG-containing streams (aqueous-based stream 112/212) and treated MPG-containing streams (aqueous extraction stream 122/222, coalesced aqueous extraction stream 232, and isolated MPG-containing stream 251). As the purity of level of MPG in each of these streams may be less than the purity level of a clean MPG, the amount of the streams used in the Mo-based catalyst preparation reactions will depend on the concentration of MPG. Thus, a smaller amount of the isolated MPG-containing stream 251 would be utilized in the reactions compared to aqueous-based stream 112/212 which has a lower MPG content. Regardless of the volume of untreated and treated MPG-containing streams used, the weight ratio of molybdenum metal to MPG will be between about 1:50 to about 1:200 before the catalyst reaction occurs.

Using these systems and the disclosed catalyst preparation methods, the cost of the POTBA process can be reduced due by using MPG sourced from a purge stream from the POSM process without affecting the performance of the molybdenum-based catalyst used for the POTBA process. This leads to a more cost-effective process for generating greater amounts of PO.

EXAMPLES

The following examples are included to demonstrate embodiments of the appended claims using the above described systems and methods of catalyst preparation. These examples are intended to be illustrative only, and not to unduly limit the scope of the appended claims. Those of skill in the art should appreciate that many changes can be made in the specific embodiments which are disclosed and still obtain a like or similar result without departing from the spirit and scope of the disclosure herein. In no way should the following examples be read to limit, or to define, the scope of the appended claims.

MPG. The following examples utilized one of three MPG sources: commercially available pure MPG (at least 99 wt % MPG), an untreated MPG purge stream from a POSM process, or a treated MPG purge stream from a POSM process.

The commercially available pure MPG was used for each comparative catalyst solution.

An MPG-containing stream exiting a settling tank from the system depicted in FIG. 1 was the untreated MPG purge stream from the POSM process used in the following examples. The composition of the untreated MPG purge stream is provided in Table 1.

TABLE 1

Composition of Untreated MPG Purge Stream

| Component | Mass Fraction (wt. %) |
|---|---|
| MPG | 38.2 |
| Water | 19.0 |
| Other heavier organic chemicals | 42.8 |

A treated MPG purge stream for use in the following examples was prepared by performing a single liquid-liquid extraction on the above untreated MPG purge stream with ethyl benzene (1:1 ratio) at ambient temperature and atmospheric pressure, similar to the liquid-liquid extraction unit 120 from the system depicted in FIG. 1. The water in the resulting aqueous extraction stream was then reduced using a 20 tray, 1-in internal diameter, glass Oldersaw vacuum distillation column at 25 mmHg. The composition of the treated MPG purge stream is provided in Table 2.

TABLE 2

Composition of Treated MPG Purge Stream

| Component | Mass Fraction (wt. %) |
|---|---|
| MPG | 82.3 |
| Water | 2.7 |
| Other heavier organic chemicals | 15 |

Instrumentation: X-Ray Fluorescence (XRF) was used to determine the concentration of the molybdenum in the final catalyst solutions. In addition to XRF, a Gas Chromatography (GC) system equipped with a Flame Ionization Detector (FID) was utilized to evaluate the epoxidation reactions.

Example 1

A series of molybdenum-based epoxidation catalysts that can be used for the POTBA process were prepared using both the untreated and treated MPG purge stream and the reagent grade MPG as described below:

Catalyst 1. To prepare Catalyst 1, 0.6 grams of molybdenum metal powder, 15 grams of the untreated MPG purge stream (38.2% MPG), 7.5 grams of t-butyl hydroperoxide (TBHP), and 60 grams of TBA were added to a reflux reactor. The reaction mixture was heated up to 60° C. under constant stirring for 3 hours. The final concentration of molybdenum in Catalyst 1 was 7600 ppm.

Catalyst 2. To prepare Catalyst 2, 0.6 grams of molybdenum metal powder, 7.5 grams of the treated MPG purge stream (82.3% MPG), 7.5 grams of TBHP, and 60 grams of TBA were added to a reflux reactor. The reaction mixture was heated up to 60° C. under constant stirring for 6 hours. The final concentration of molybdenum in Catalyst 2 was 8200 ppm.

Comparative Catalyst 1. To prepare Comparative Catalyst 1, 0.6 grams of molybdenum metal powder, 7.5 grams of the reagent grade MPG (>99% MPG), 7.5 grams of TBHP, and 60 grams of TBA were added to a reflux reactor. The reaction mixture was heated up to 60° C. under constant stirring for 6 hours, two times longer than the time needed for Catalyst 1. The final concentration of molybdenum in Comparative Catalyst 1 was 7800 ppm.

Comparative Catalyst 2. To prepare Comparative Catalyst 2, 0.6 grams of molybdenum metal powder, 7.5 grams of the reagent grade MPG (>99% MPG), 3.75 grams of deionized water, 7.5 grams of TBHP, and 60 grams of TBA were added to a reflux reactor. The reaction mixture was heated up to 60° C. under constant stirring for 2.25 hours. The final concentration of molybdenum in Comparative Catalyst 2 was 8400 ppm.

Comparative Catalyst 3. To prepare Comparative Catalyst 3, 0.6 grams of molybdenum metal powder, 7.5 grams of the reagent grade MPG (>99% MPG), 7.5 grams of deionized water, 7.5 grams of TBHP, and 60 grams of TBA were added to a reflux reactor. The reaction mixture was heated up to 60° C. under constant stirring for 2.25 hours. The final concentration of molybdenum in Comparative Catalyst 3 was 7600 ppm.

Comparative Catalyst 4. To prepare Comparative Catalyst 4, 0.6 grams of molybdenum metal powder, 7.5 grams of the reagent grade MPG (>99% MPG), 11 grams of deionized water, 7.5 grams of TBHP, and 60 grams of TBA were added to a reflux reactor. The reaction mixture was heated up to 60° C. under constant stirring for 1.5 hours. The final concentration of molybdenum in Comparative Catalyst 4 was 7700 ppm.

Comparative Catalyst 5. To prepare Comparative Catalyst 5, 0.6 grams of molybdenum metal powder, 7.5 grams of the reagent grade MPG (>99% MPG), 25 grams of deionized water, 7.5 grams of TBHP, and 60 grams of TBA were added to a reflux reactor. The reaction mixture was heated up to 60° C. under constant stirring for 1 hour. The final concentration of molybdenum in Comparative Catalyst 5 was 6000 ppm.

Once the reactions were complete, the catalyst reaction mixture was filtered to remove undissolved metallic molybdenum.

Reagent grade MPG was used in place of the PO SM-sourced MPG for Comparative Catalysts 1-5 to remove any influences from impurities in those streams. Further, Comparative Catalyst 1 was prepared without water per conventional methods. Comparative Catalyst 2-5 were prepared with the addition of varying amounts of deionized water to evaluate the effect of water on the catalyst preparation methods.

The reaction time for preparing a catalyst increased when less water was present, as shown in Table 3. Comparative Catalyst 1 has a reaction time of 6 hours, compared to the 2.25 hours reaction time for Comparative Catalyst 2 and the 1 hour reaction time needed by Comparative Catalyst 5.

TABLE 3

Comparison of reaction time and water content in the catalyst reaction mixture

| Catalyst | Amount of Water Added | Reaction time at 60° C. (hours) |
|---|---|---|
| Comparative Catalyst 1 | 0 | 6 |
| Comparative Catalyst 2 | 3.75 g | 2.25 |
| Comparative Catalyst 3 | 7.5 g | 2.25 |
| Comparative Catalyst 4 | 11 g | 1.5 |
| Comparative Catalyst 5 | 25 g | 1 |

Similar results were also seen with Catalyst 1 and 2. The water in both reaction mixtures came from the purge stream. Catalyst 1 used an untreated MPG-containing stream having 19 wt % of water, resulting in a reaction time of 3 hours. Catalyst 2, however, used a treated MPG purge stream having a water content of 2.7 wt %, leading to a reaction time of 6 hours.

The molybdenum concentrations in the final catalyst were evaluated using XRF after the unreacted molybdenum metal was filtered out. The final concentration of molybdenum varied with the water content in the initial reaction, as shown in Table 4. Lower amounts of water in the initial catalyst reaction mixture led to a higher concentration of molybdenum in the final catalyst. The amount of molybdenum in the final catalyst did increase with the addition of 3.75 grams of water in Comparative Catalyst 2. However, increasing water content led to a smaller concentration of Molybdenum due to its dilution, as seen in Comparative Catalyst 3, 4, and 5.

TABLE 4

Comparison of Molybdenum in the final catalyst and water content in the initial catalyst reaction mixture

| Catalyst | Amount of Water Added to Catalyst Reaction Mixture | Concentration* of Molybdenum in the final Catalyst (ppm) |
| --- | --- | --- |
| Comparative Catalyst 1 | 0 | 7800 |
| Comparative Catalyst 2 | 3.75 g | 8400 |
| Comparative Catalyst 3 | 7.5 g | 7600 |
| Comparative Catalyst 4 | 11 g | 7600 |
| Comparative Catalyst 5 | 25 g | 6600 |

*As determined by XRF

Example 2

The catalysts prepared in Example 1 were evaluated as epoxidation catalysts for the POTBA process.

For the POTBA propylene epoxidation process, 5 grams of a catalyst prepared in Example 1 was combined with 60 grams of propylene, and 120 grams of TBHP oxidate (30 wt % in TBA) in a batch reactor. A 1.2 g aliquot of n-octane was also added to the reactor as an internal standard.

The batch reactor was pressurized and heated up to 110° C. After 2 hours, the final mixture was analyzed to calculate the remaining TBHP and the PO product formed. Table 5 displays the results.

TABLE 5

Epoxidation results using the catalysts prepared in Example 1

| Catalyst | Concentration* of Molybdenum (ppm) in the catalyst | TBHP Conversion‡ (%) | PO formed‡ (grams) |
| --- | --- | --- | --- |
| Catalyst 1 | 7600 | 90.1 | 22.0 |
| Catalyst 2 | 8200 | 91.0 | 21.9 |
| Comp. Catalyst 1 | 7800 | 90.2 | 23.5 |
| Comp. Catalyst 2 | 8400 | 90.3 | 20.8 |
| Comp. Catalyst 3 | 7600 | 90.3 | 23.1 |
| Comp. Catalyst 4 | 7600 | 89.0 | 25.6 |
| Comp. Catalyst 5 | 6600 | 88.6 | 18.4 |

*As determined by XRF
‡As determined by GC-FID

The use of MPG sourced from the POSM process did not affect the performance of Catalyst 1 and 2. Both catalysts formed about 22 grams of PO. Further, no significant difference in conversion or PO formation were seen with Comparative Catalysts 1-5. Though Comparative Catalyst 5 has the lowest conversion of TBHP and PO formed, this catalyst also had the highest concentration of water resulting in a more dilute molybdenum concentration than the other Comparative Catalyst. In some systems, this conversion rate may be acceptable as it offsets the cost of reducing the water content of the MPG-containing stream.

The above examples show that it is possible to maintain catalytic activity for molybdenum-based epoxidation catalyst prepared using MPG sourced from purge streams from a POSM process. Utilizing MPG from POSM purge streams also reduces costs and equipment needed to treat these streams. This ability to prepare epoxidation catalysts while reducing capital costs and energy consumption for recycling POSM purge streams provides for an efficient POTBA process to meet the global demands for PO and its derivative polyurethanes.

The following references are incorporated by reference in their entirety.
U.S. Ser. No. 62/844,539, filed May 7, 2019
U.S. Pat. No. 3,434,975

What is claimed is:

1. A molybdenum epoxidation catalyst composition, comprising:
   a) molybdenum metal powder;
   b) a peroxy compound;
   c) a solvent; and,
   d) a stream containing monopropylene glycol (MPG), wherein the stream containing monopropylene glycol is derived from a purge stream of a Propylene Oxide/Styrene Monomer (POSM) production process, wherein the stream containing monopropylene glycol comprises water.

2. The molybdenum epoxidation catalyst composition of claim 1, wherein the MPG is present in an amount of about 1 to about 15 weight percent based on the total weight of the molybdenum epoxidation catalyst composition.

3. The molybdenum epoxidation catalyst composition of claim 1, wherein the stream containing monopropylene glycol contains 25 to 75 wt. % of monopropylene glycol, 15 to 75 wt. % of water, and 1 to 50 wt. % of organic compounds.

4. The molybdenum epoxidation catalyst composition of claim 1, wherein the stream containing monopropylene glycol contains 5 to 75 wt. % of water.

5. The molybdenum epoxidation catalyst composition of claim 1, wherein a weight ratio of the molybdenum metal powder to the peroxy compound is between about 1:5 to 1:20, a weight ratio of the molybdenum metal powder to the solvent is between about 1:50 to 1:200, and a weight ratio of the molybdenum metal powder to the MPG is between about 1:50 to about 1:200.

6. The molybdenum epoxidation catalyst composition of claim 5, wherein the peroxy compound is t-butyl hydroperoxide (TBHP).

7. The molybdenum epoxidation catalyst composition of claim 5, wherein the solvent is t-butyl alcohol (TBA).

8. The molybdenum epoxidation catalyst composition of claim 5, wherein the molybdenum metal powder is present in an amount of about 0.5 to 1.0 grams, the peroxy compound is present in an amount of about 5 to 10 grams, and the TBA is present in an amount of about 50 to 100 grams.

9. A method for preparing a molybdenum-based epoxidation catalyst, said method comprising:
   a) forming the molybdenum epoxidation catalyst composition of claim 1 comprising:

i) feeding the monopropylene glycol (MPG)-containing stream into a reactor, wherein said the MPG-containing stream is the purge stream from the Propylene Oxide/Styrene Monomer (POSM) production process;

ii) adding the molybdenum metal powder, the peroxy compound, and the solvent to said reactor;

b) reacting a mixture of the molybdenum metal powder, the peroxy compound, the solvent and the MPG-containing stream to produce the molybdenum epoxidation catalyst; and c) isolating said molybdenum epoxidation catalyst from other reaction products.

10. The method of claim 9, wherein at least one of the MPG-containing purge stream has been treated to concentrate the MPG before being fed into said reactor.

11. The method of claim 9, wherein a total concentration of the MPG in the purge stream is from about 30 to about 75 weight percent.

12. The method of claim 9, wherein an amount of the MPG in the reaction mixture is from about 1 to about 15 weight percent.

13. The method of claim 9, wherein a weight ratio of the molybdenum metal powder to the peroxy compound is between about 1:5 to 1:20, a weight ratio of the molybdenum metal powder to the solvent is between about 1:50 to 1:200, and a weight ratio of the molybdenum metal powder to the MPG is between about 1:50 to about 1:200.

14. A method for preparing a molybdenum epoxidation catalyst, the method comprising:
a) forming the molybdenum epoxidation catalyst composition of claim 1 comprising:
i) preparing the monopropylene glycol (MPG)-containing stream from at least one exit stream recovered from the POSM process in a POSM reactor, wherein said preparing step comprises;
1) directing one or more streams exiting the POSM reactor into a settling tank to separate the one or more exit streams into an aqueous-based purge stream and an organic-based purge stream, wherein the aqueous-based purge stream comprises (i) mono-propylene glycol, and (ii) a first amount of α-methyl benzyl alcohol, a first amount of benzaldehyde, a first amount of acetophenone, or a combination thereof;
ii) feeding said MPG-containing stream into a reactor;
iii) adding the molybdenum metal powder, the peroxy compound, and the solvent to said reactor to form a reaction mixture;
b) reacting the reaction mixture in the reactor to produce a molybdenum epoxidation catalyst; and
c) isolating said molybdenum epoxidation catalyst from other reaction products.

15. The method of claim 14, wherein said preparing step further comprises:
ii) contacting the aqueous-based purge stream with an organic extraction liquid in a liquid-liquid extraction unit to form an aqueous-based extraction stream and an organic extraction stream;
iii) wherein the aqueous-based extraction stream comprises (i) mono-propylene glycol, and (ii) a second amount of α-methyl benzyl alcohol, a second amount of benzaldehyde, a second amount of acetophenone, or a combination thereof, wherein, the second amount of α-methyl benzyl alcohol, the second amount of benzaldehyde, and the second amount of acetophenone are less than the first amount of α-methyl benzyl alcohol, the first amount of benzaldehyde, and the first amount of acetophenone, respectively.

16. The method of claim 15, wherein said preparing step further comprises:
iv) concentrating the MPG in the aqueous-based extraction stream by coalescing said aqueous-based extraction stream in a coalescer, treating a coalesced output with activated carbon, and drying with a drying apparatus.

17. The method of claim 14, wherein a total concentration of the MPG in the MPG-containing stream is from about 30 to about 75 weight percent.

18. The method of claim 14, wherein an amount of the MPG in the reaction mixture is from about 1 to about 15 weight percent.

19. The method of claim 14, wherein a weight ratio of the molybdenum metal powder to the peroxy compound is between about 1:5 to 1:20, a weight ratio of the molybdenum metal powder to the solvent is between about 1:50 to 1:200, and a weight ratio of the molybdenum metal powder to the MPG is between about 1:50 to about 1:200.

20. The method of claim 14, wherein the organic extraction liquid is ethylbenzene, toluene, n-octane, or combinations thereof.

* * * * *